US012808827B2

(12) United States Patent
Yoon et al.

(10) Patent No.: US 12,808,827 B2
(45) Date of Patent: Nov. 24, 2026

(54) SUSPENDED NANOWIRE STRUCTURE CAPABLE OF HIGH-SPEED OPERATION

(71) Applicant: KOREA ADVANCED INSTITUTE OF SCIENCE AND TECHNOLOGY, Daejeon (KR)

(72) Inventors: Jun-Bo Yoon, Daejeon (KR); Min-Seung Jo, Daejeon (KR); Jae Shin Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 948 days.

(21) Appl. No.: 17/678,644

(22) Filed: Feb. 23, 2022

(65) Prior Publication Data

US 2023/0106878 A1 Apr. 6, 2023

(30) Foreign Application Priority Data

Oct. 5, 2021 (KR) ........................ 10-2021-0131930

(51) Int. Cl.
*G01N 27/12* (2006.01)
*G01N 33/00* (2006.01)

(52) U.S. Cl.
CPC ......... *G01N 27/128* (2013.01); *G01N 27/127* (2013.01); *G01N 33/005* (2013.01)

(58) Field of Classification Search
CPC .. G01N 27/128; G01N 27/127; G01N 33/005; B82B 1/005; B82B 3/0014;
(Continued)

(56) References Cited

U.S. PATENT DOCUMENTS 6,161,421 A * 12/2000 Fang .................... G01N 27/128 73/23.31
7,861,575 B2 * 1/2011 Jun .................... G01N 33/0027 73/25.05

(Continued)

FOREIGN PATENT DOCUMENTS

KR 1020160031147 A 3/2016
KR 102218984 B 2/2021

OTHER PUBLICATIONS

"Perfectly Aligned, Air-Suspended Nanowire Array Heater and Its Application in an Always-On Gas Sensor." Advanced Functional Materials, vol. 30, Issue 39. First published on Aug. 12, 2020 (Year: 2020).*

(Continued)

*Primary Examiner* — Maris R Kessel
*Assistant Examiner* — May Leung Chiu
(74) *Attorney, Agent, or Firm* — Foley & Lardner LLP

(57) ABSTRACT

The present invention relates to a suspended nanowire structure. The present invention, more particularly, relates to a suspended nanowire structure capable of high-speed operation by improving the reaction rate by making the temperature distribution of the nanowire uniform.

A suspended nanowire structure in accordance with an embodiment of the present invention comprises: a substrate; a plurality of nanowires float on the substrate and extending along a first direction; electrodes respectively connected to both ends of the plurality of nanowires; and a heating electrode which is disposed on both ends of the plurality of nanowires, extends in a second direction perpendicular to the first direction, and provides heat to both ends of the plurality of nanowires during driving.

12 Claims, 11 Drawing Sheets

(58) Field of Classification Search
CPC ......... B82B 3/0061; G03F 7/16; B82Y 15/00; B82Y 40/00
See application file for complete search history.

(56) References Cited

U.S. PATENT DOCUMENTS

| | | | | |
|---|---|---|---|---|
| 10,788,470 | B2 * | 9/2020 | Toffoli | G01N 30/95 |
| 2015/0247828 | A1 * | 9/2015 | Ruellan | G01N 27/18 73/25.05 |
| 2020/0041447 | A1 * | 2/2020 | Chang | H10D 48/30 |
| 2020/0240942 | A1 * | 7/2020 | Prajapati | G01N 27/128 |

OTHER PUBLICATIONS

"Stress-engineered palladium nanowires for wide range (0.1%-3. 9%) of H2 detection with high durability." Nanoscale, 2019, 11, 16317-16326 (Year: 2019).*

Jiang et al. "Integrated Temperature and Hydrogen Sensors with MEMS Technology." Sensors 2018, 18(1), 94) (Year: 2017).*

RamÃ-rez et al. (Architecture for the efficient manufacturing by printing of heated, planar, resistive transducers on polymeric foil for gas sensing. Sensors and Actuators B: Chemical. Volume 258, Apr. 1, 2018, pp. 952-960 (Year: 2018).*

Korean Office Action issued in corresponding Korean Patent Application No. 10-2021-0131930, dated Apr. 25, 2023 with English machine translation (8 pages).

* cited by examiner hydrogen sensor performance index based on U.S. Department of Energy (DoE)

| Parameter | Safety Systems[1] |
|---|---|
| Measurement Range | 0.1% - 10% |
| Detection Limit | - |
| Operating Temperature | -30 °C ~ 80 °C |
| Response Time | < 1 s |
| Recovery Time | - |
| Accuracy | 5% |

SUSPENDED NANOWIRE STRUCTURE CAPABLE OF HIGH-SPEED OPERATION

CROSS-REFERENCE TO RELATED APPLICATIONS

This application claims priority to and the benefit of Korean Patent Application No. 10-2021-0131930 filed in the Korean Intellectual Property Office on Oct. 5, 2021, the entire contents of which are incorporated herein by reference.

TECHNICAL FIELD

The present invention relates to a suspended nanowire structure. The present invention, more particularly, relates to a suspended nanowire structure capable of high-speed operation by improving the reaction rate by making the temperature distribution of the nanowire uniform.

BACKGROUND ART

Hydrogen is an eco-friendly energy carrier. Hydrogen has 2.6 times higher combustion energy than regular gasoline. Hydrogen is being used or planned to be used in various applied vehicles, energy storage, and batteries, and a lot of research is currently underway.

The hydrogen gas sensor is a sensor that senses hydrogen gas. Since hydrogen gas is a colorless, odorless gas and has high explosiveness (4 to 75% inair), a hydrogen gas sensor capable of accurately and rapidly sensing hydrogen gas is required.

FIG. 1 shows a conventional gas sensor and a hydrogen sensor performance index based on U.S. DoE.

In general, palladium (Pd) is widely used as a gas sensor because it selectively and actively reacts with hydrogen. In particular, as shown in the upper figure of FIG. 1, nanomaterial nanowires and nanoparticles using palladium (Pd) have excellent gas reactivity due to a high volume-to-surface area ratio, and thus are widely used in gas sensors.

However, the conventional gas sensor still has a slow response rate of several tens of seconds (sec), which still does not meet the standards of the US Department of Energy (DoE) hydrogen sensor performance index.

FIGS. 2 to 3 are diagrams for explaining a high-temperature heating method of a conventional gas sensor.

The high-temperature heating method of the conventional gas sensor shown in FIG. 2 is a structure in which an electrode design is not considered, and the high-temperature heating method of the conventional gas sensor shown in FIG. 3 has a structure in which a heating element (heater) and a sensing element are vertically stacked. FIGS. 4 to 5 are diagrams for explaining a conventional suspended nanowire structure.

The suspended nanowire structure shown in FIG. 4 is disclosed in Patent Document 1 which discloses manufacturing technology and design for stably suspended nanowires in the air.

The advantages of a suspended nanowire structure will be described in comparison with a general nanowire structure with reference to FIG. 5. In a general nanowire structure, a plurality of nanowires are disposed on an upper surface of a substrate. On the other hand, in the suspended nanowire structure, multiple suspended nanowires are disposed to float in the air at a predetermined distance from the upper surface of the substrate.

In a general nanowire structure, a plurality of nanowires are in direct contact with the upper surface of the substrate. Therefore, there are problems in that a contact part with an external gas is small, heat generated from a plurality of nanowires is easily discharged to a substrate, and interfacial interference occurs. On the other hand, in the case of an suspended nanowire structure, a plurality of suspended nanowires are disposed to be spaced apart from the upper surface of the substrate. Therefore, a contact area with external gas is large, heat generated from a plurality of suspended nanowires is difficult to escape to the substrate, thereby enabling efficient heating, and since a plurality of suspended nanowires and the substrate are independent of each other, interface interference may not occur. In particular, there is a characteristic that thermal, mechanical, electrical, and chemical influences by the substrate are blocked.

FIGS. 6 to 8 are views for describing a conventional aerial suspended nanowire structure having nanowires made of palladium and characteristics thereof.

Referring to FIG. 6, a plurality of nanowires of a conventional air-rich nanowire structure are formed of a palladium material, the plurality of nanowires are connected to an aluminum electrode at both ends thereof, and are disposed suspended in the air from an upper surface of a substrate. The conventional suspended nanowire structure achieves a high reaction speed when operated at a high temperature by a self-heating method, but still has a slow reaction speed even when operated at a high temperature above 80° C. as shown in FIG. 7.

Referring to FIG. 8, since the total reaction rate of the suspended nanowire structure is determined by the part having the lowest temperature of the nanowire, it is important that the entire nanowire is uniform as a high temperature.

PRIOR ART LITERATURE

Patent Literature (Patent Document 1) KR 10-2218984 B1

SUMMARY OF THE INVENTION

The problem to be solved by the present invention is to provide a suspended nanowire structure capable of high-speed operation by increasing the reaction speed during operation.

In addition, the present invention provides a suspended nanowire structure capable of uniformizing the overall temperature of the nanowires at high temperatures.

A suspended nanowire structure in accordance with an embodiment of the present invention comprises: a substrate; a plurality of nanowires float on the substrate and extending along a first direction; electrodes respectively connected to both ends of the plurality of nanowires; and a heating electrode which is disposed on both ends of the plurality of nanowires, extends in a second direction perpendicular to the first direction, and provides heat to both ends of the plurality of nanowires during driving.

A suspended nanowire structure in accordance with another embodiment of the present invention comprises: a substrate; a plurality of nanowires float on the substrate and extending along a first direction; first electrodes for heating element disposed at both ends of the plurality of nanowires, respectively, and heating elements which have one end connected to the first electrode for heating element, are horizontally disposed with the plurality of nanowires, and provide heat to both ends of the plurality of nanowires.

According to the suspended nanowire structure according to the embodiment of the present invention, there is an advantage that high-speed operation is possible by increasing the reaction speed during operation. In particular, there is an advantage in that the sensing speed of the gas can be improved.

In addition, there is an advantage in that the overall temperature of the nanowire may be uniform at a high temperature.

DETAILED DESCRIPTION

Figure 1:
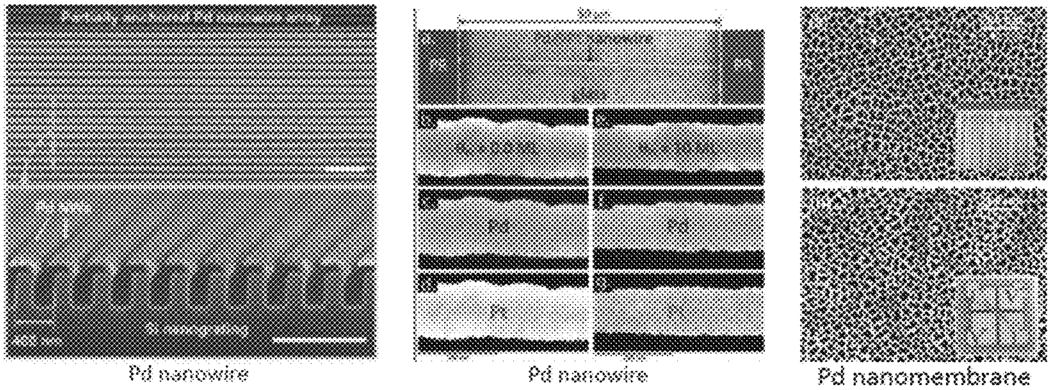
FIG. 1 (Prior Art)
FIG. 1 shows a conventional gas sensor and a hydrogen sensor performance index based on U.S. DoE.
Figure 2:
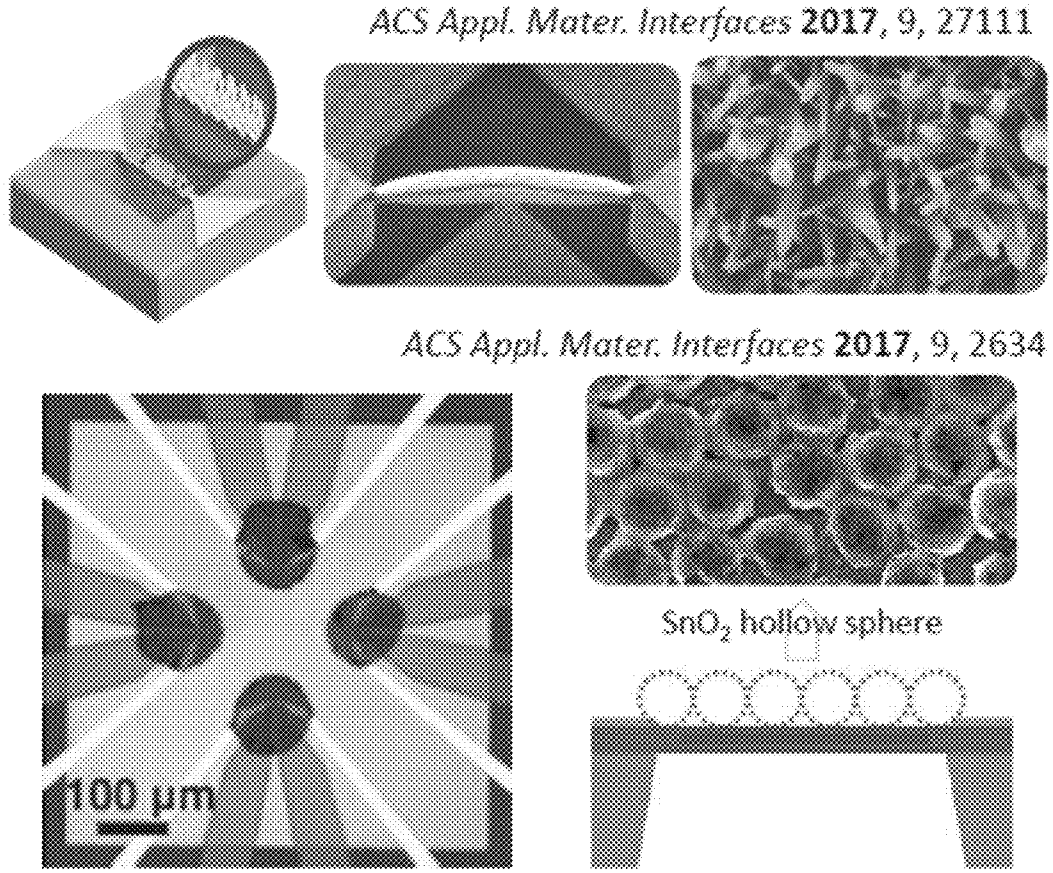
FIG. 2 (Prior Art)
FIGS. 2 to 3 are diagrams illustrating a high-temperature heating method of a conventional gas sensor.
Figure 3:
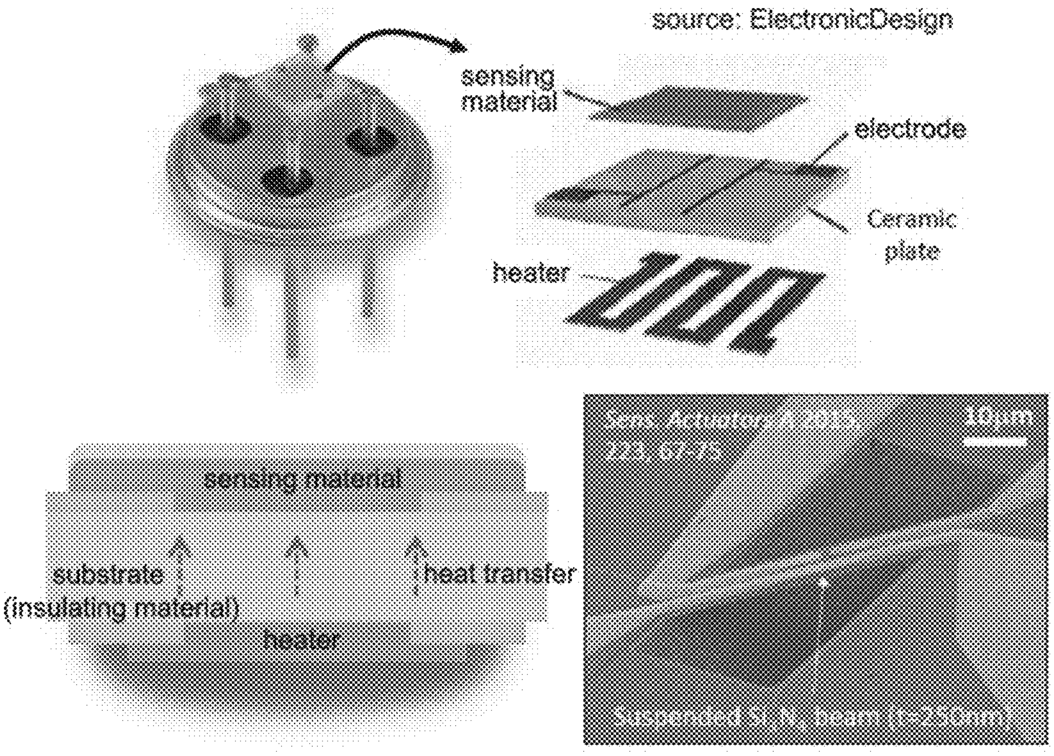
FIG. 3 (Prior Art)
Figure 4:
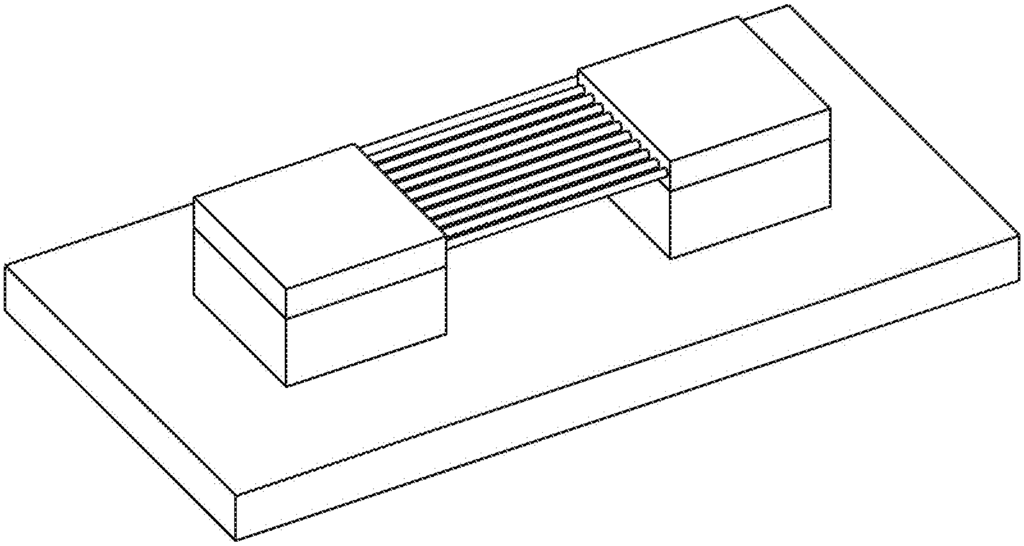
FIG. 4 (Prior Art)
FIGS. 4 to 5 are diagrams for explaining a conventional suspended nanowire structure.
Figure 5:
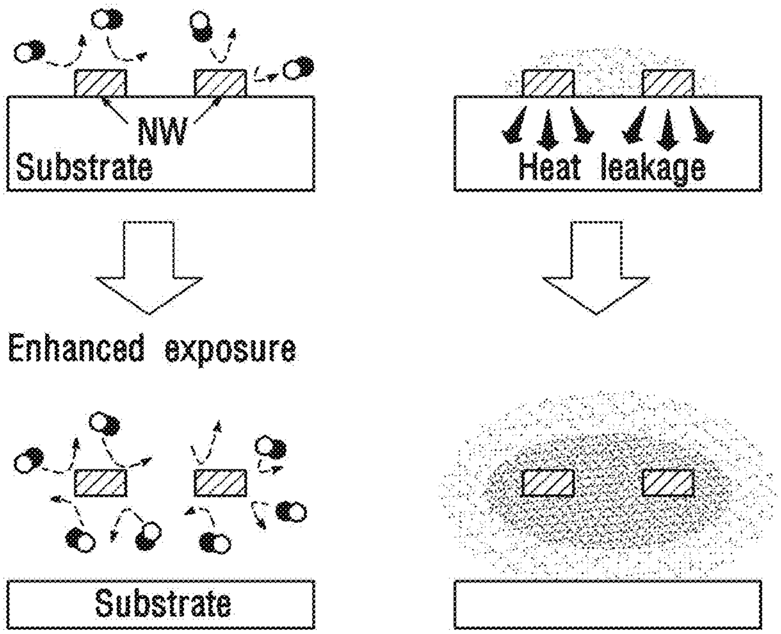
FIG. 5 (Prior Art)
Figure 6:
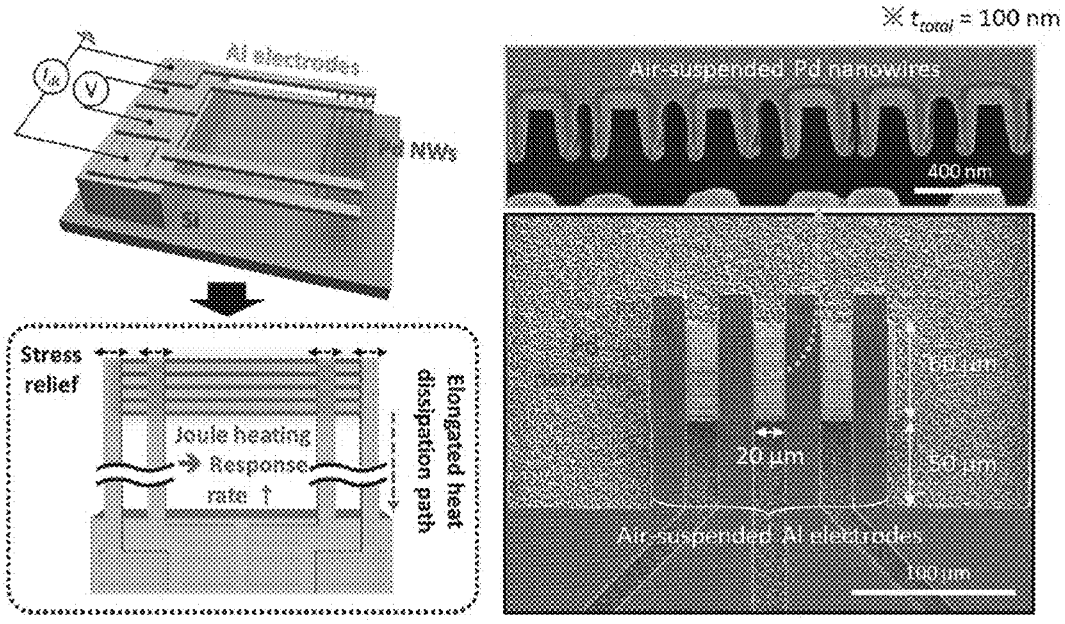
FIG. 6 (Prior Art)
FIGS. 6 to 8 are views for describing a conventional suspended nanowire structure having nanowires made of palladium and characteristics thereof.
Figure 7:
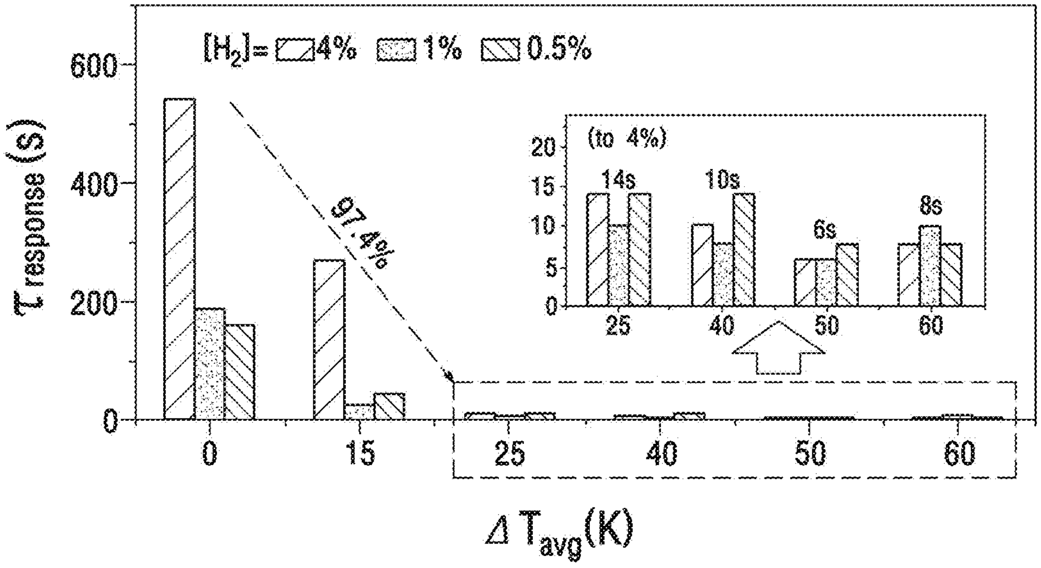
FIG. 7 (Prior Art)

The detailed description of the present invention, which will be described later, is referred to the accompanying drawings illustrating a specific embodiment in which the present invention may be implemented as an example. These embodiments are described in detail sufficiently so that those skilled in the art may implement the present invention. It should be understood that various embodiments of the present invention are different from each other, but need not be mutually exclusive. For example, specific shapes, structures, and characteristics described herein may be implemented in other embodiments without departing from the spirit and scope of the present invention in relation to one embodiment. In addition, it should be understood that the location or arrangement of individual components within each disclosed embodiment may be changed without departing from the spirit and scope of the present invention. Therefore, the detailed description to be described below is not limited in meaning, and the scope of the present invention is limited only by the appended claims as well as all ranges equivalent to those claimed in the claims, if appropriate. In the drawings, similar reference numerals refer to the same or similar functions across several aspects.

Figure 9:
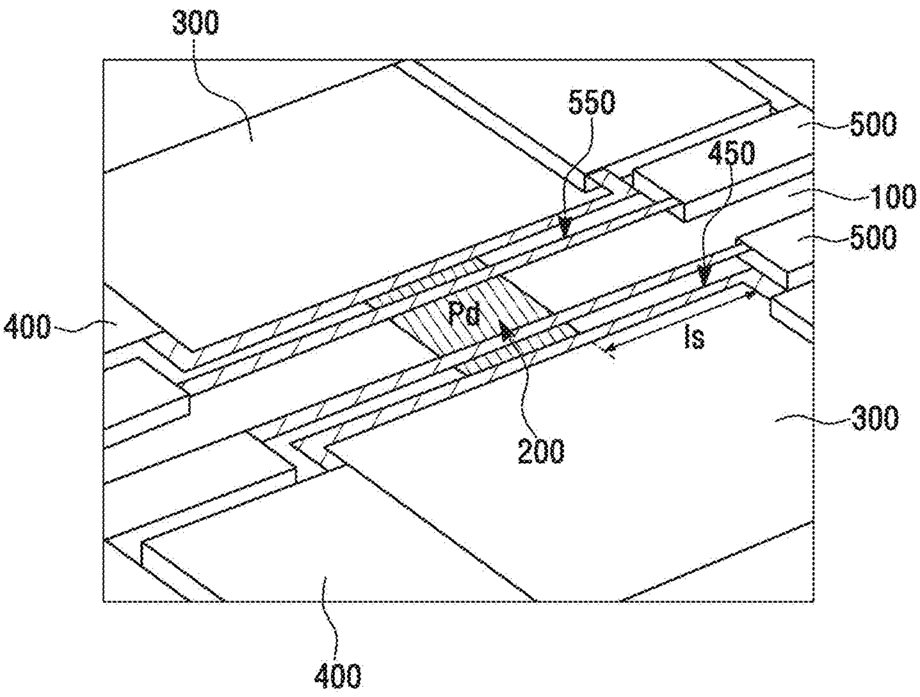
FIG. 9 is an enlarged perspective view of a portion of a suspended nanowire structure according to an embodiment of the present invention.
Figure 10:
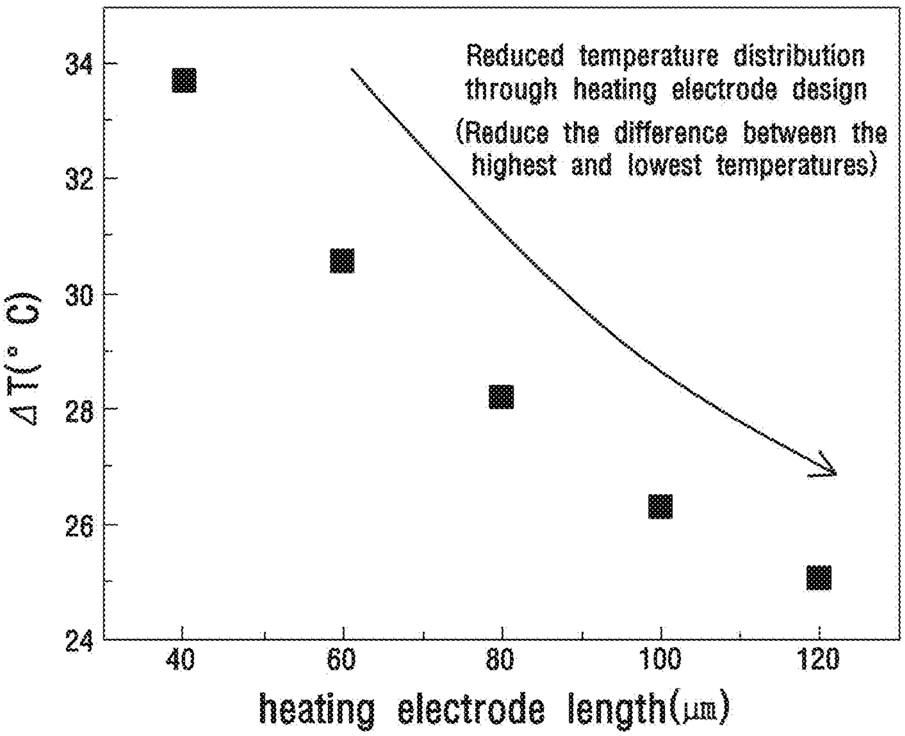
FIG. 10 is a graph illustrating a temperature change with respect to a length of a heating electrode in the suspended nanowire structure shown in FIG. 9.

FIG. 9 is an enlarged perspective view of a portion of the suspended nanowire structure according to an embodiment of the present invention, and FIG. 10 is a graph showing a temperature change with respect to a length of a heating electrode in the suspended nanowire structure shown in FIG. 9.

Figure 8:
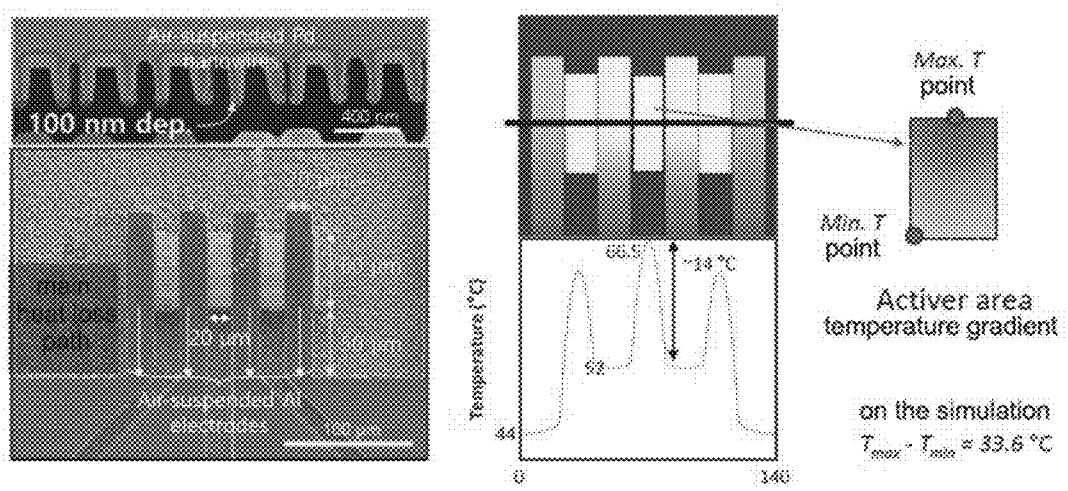
FIG. 8 (Prior Art)

First, the reason why each nanowire of the conventional suspended nanowire structure shown in FIG. 8 is not uniformly distributed is that the nanowire loses heat through an electrode connected to both ends of the nanowire made of palladium (Pd).

In order to solve this problem, the suspended nanowire structure according to an embodiment of the present invention shown in FIG. 9 may introduce a heating electrode to supplement heat lost from both ends of each nanowire to the electrode.

In the suspended nanowire structure shown in FIG. 9 according to an embodiment of the present invention, the main heat loss path is reduced, and thus the overall temperature distribution of each nanowire may be reduced compared to the conventional suspended nanowire structure.

Hereinafter, a structure of a suspended nanowire structure according to an embodiment of the present invention will be described in detail.

Referring to FIG. 9, the suspended nanowire structure according to an embodiment of the present invention may include: a substrate 100; a plurality of nanowires 200; electrodes 300; a heating electrode 450; and an electrode for heating 400.

A plurality of nanowires 200 float on the substrate 100 and extend along a first direction. Each nanowire 200 may be made of a gas sensing material. Specifically, each nanowire 200 may be made of a metal material, for example, palladium (Pd), Pd-metal alloy, or Pd based compound. In addition, each nanowire 200 may be formed of, for example, a metal oxide ($SnO2$, ZnO) or silicon (Si) as a semiconductor material.

Meanwhile, in FIG. 9, a plurality of nanowires 200 are illustrated in a film form, but this is schematically illustrated for simulation. Here, the plurality of nanowires 200 may be replaced with a metal film as shown in FIG. 9. The structure including the metal film may be referred to as a suspended film structure.

The electrodes 300 are connected to both ends of a plurality of nanowires 200, respectively. The electrodes 300 are disposed at one end and the other end of each nanowire 200. The electrodes 300 may be referred to as inner electrodes. The electrodes 300 may include a first inner electrode at a first end of the plurality of nanowires 200 and a second inner electrode at a second end of the plurality of nanowires 200.

The heating electrodes 450 are disposed on both ends of the plurality of nanowires 200 and extend along a second direction perpendicular to the first direction which is an extending direction of the nanowires 200. In FIG. 9, the number of heating electrodes 450 is illustrated as two, but is not limited thereto. For example, two or more heating electrodes 450 may be disposed on each of both ends of the plurality of nanowires 200.

The electrodes for heating 400 are connected to both ends of the heating electrodes 450, respectively. The electrodes for heating 400 are disposed at one end and the other end of the heating electrode 450, respectively.

In the suspended nanowire structure according to an embodiment of the present invention shown in FIG. 9, heating electrodes 450 are disposed on both ends of each nanowire 200. Accordingly, during driving, heat lost to the electrode 300 at both ends of each nanowire 200 may be supplemented. Since the heat lost at both ends of each nanowire 200 is supplemented, the overall temperature distribution may be made uniform when each nanowire 200 is driven. Accordingly, temperatures at both ends, which are portions having the lowest temperature in each nanowire 200, are increased by the heating electrode 450. Therefore, it is possible to improve the reaction rate to the gas.

The suspended nanowire structure according to an embodiment of the present invention shown in FIG. 9 may further include a measurement electrode 550 extending in a second direction between two heating electrodes 450 disposed on both ends of each nanowire 200, and electrodes for measuring 500 connected to both ends of the measurement electrode 550.

As the length Is of the heating electrode 450 increases, the difference between the maximum temperature and the minimum temperature at each nanowire 200 (hereinafter, referred to as "temperature distribution") decreases. Specifically, FIG. 10 illustrates a graph of temperature change (ΔT) according to the length Is of the heating electrode 450. Referring to FIG. 10, it may be seen that the difference between the maximum temperature and the minimum temperature of each nanowire 200 decreases as the length of the heating electrode 450 increases. Here, the length Is of the heating electrode 450 may be a length from one end of the heating electrode 450 to a nanowire disposed at one edge of the plurality of nanowires 200.

Figure 11:
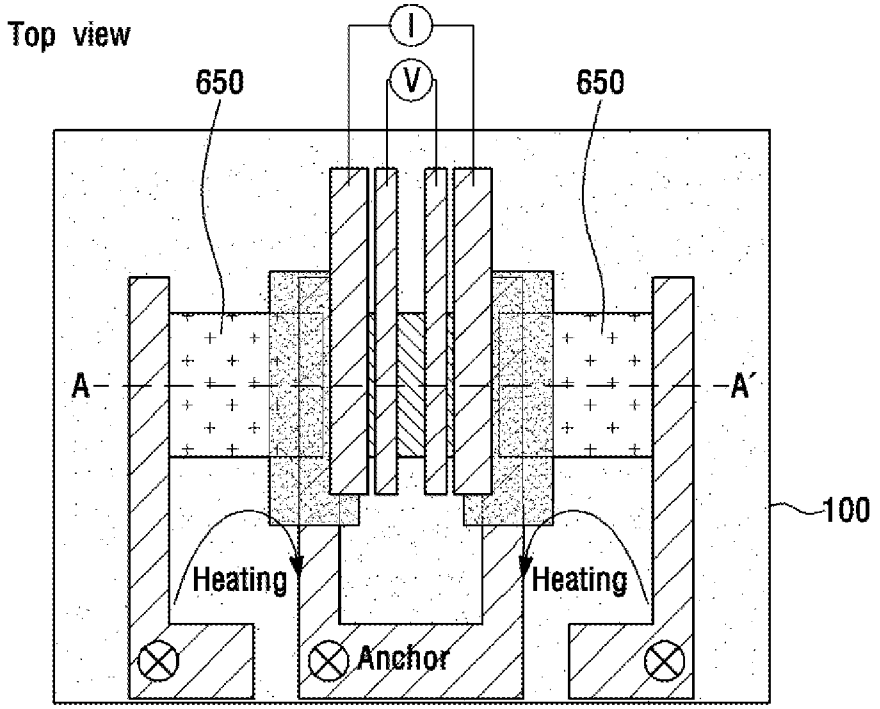
FIG. 11 is a plan view of a suspended nanowire structure according to another embodiment of the present invention.
Figure 12:
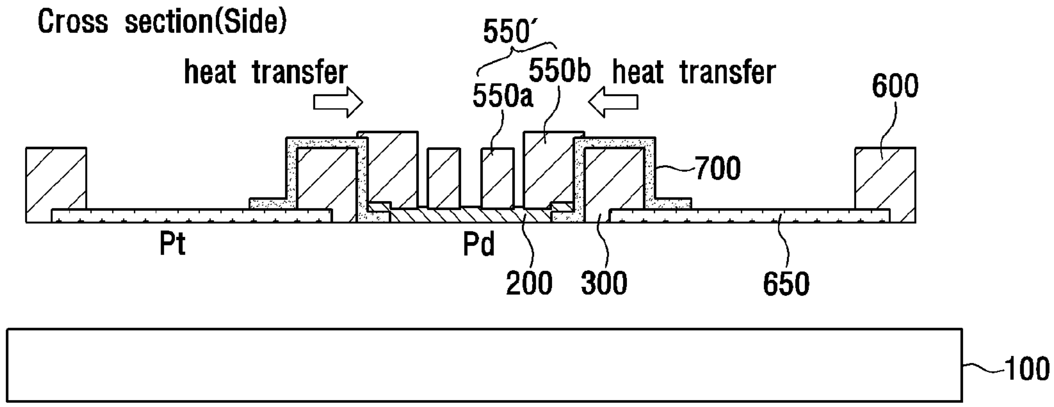
FIG. 12 is a cross-sectional view of the suspended nanowire structure illustrated in FIG. 11 as A-A'.

FIG. 11 is a plan view of a suspended nanowire structure according to another embodiment of the present invention. FIG. 12 is a cross-sectional view of the suspended nanowire structure illustrated in FIG. 11 as A-A'.

Referring to FIGS. 11 to 12, a suspended nanowire structure according to another embodiment of the present invention may include: a substrate 100; a plurality of nanowires 200; a first electrode 300 for heating element, a heating element 650, and a second electrode 600 for heating element.

A plurality of nanowires 200 float on the substrate 100 and extend along the first direction. Each nanowire 200 may be made of a gas sensing material. Specifically, each nanowire 200 may be made of a metal material, for example, palladium (Pd), Pd-metal alloy, or Pd based compound. In addition, each nanowire 200 may be formed of, for example, a metal oxide (SnO2, ZnO) or silicon (Si) as a semiconductor material.

Figure 14:
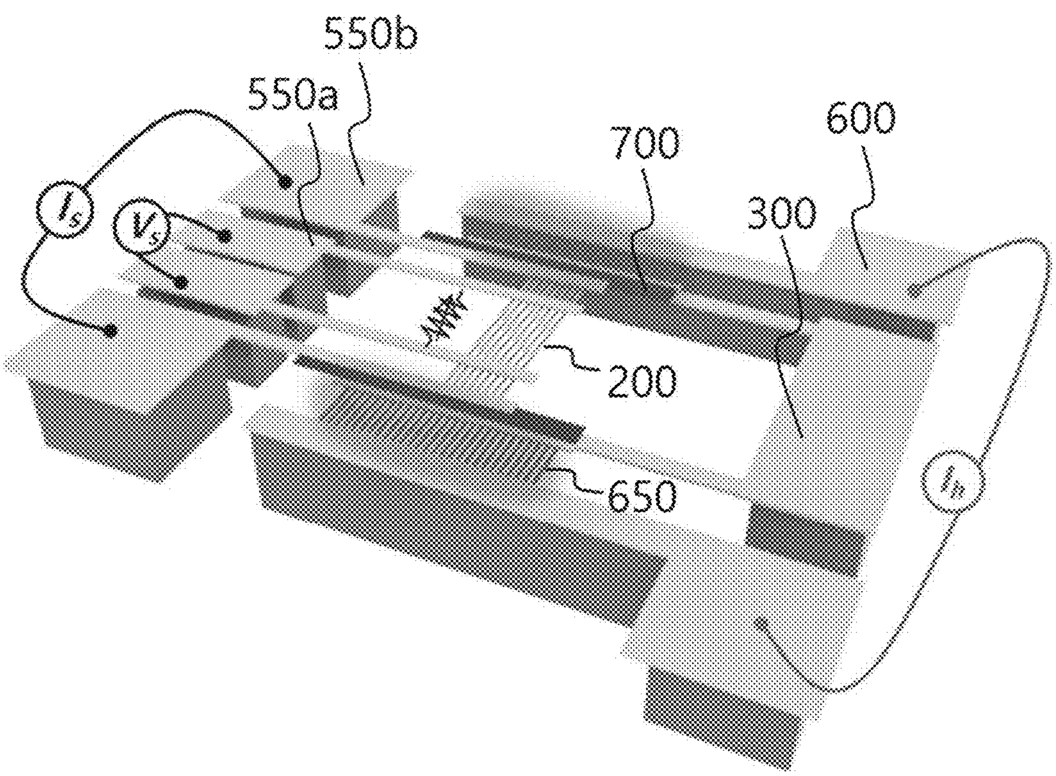
FIG. 14 is a perspective view of a suspended nanowire structure including a plurality of nanowires.

Meanwhile, in FIG. 11, a plurality of nanowires 200 are illustrated in a film form, but this is schematically illustrated for simulation, and as shown in FIG. 14, a plurality of nanowires 200 extending along the first direction may be arranged in the second direction. Here, the plurality of nanowires 200 may be replaced with a metal film as shown in FIG. 11. The structure including the metal film may be referred to as a suspended film structure.

The first electrodes 300 for heating element are disposed at both ends of the plurality of nanowires 200, respectively. The first electrode 300 for heating is disposed at one end and the other end of each nanowire 200, respectively. One end of the first electrode 300 for heating element may be fixed to the substrate 100 by an anchor.

The heating elements 650 are disposed on both sides of the plurality of nanowires 200, respectively, and is connected to the first electrode 300 for heating element. The heating element 650 and a plurality of nanowires 200 are horizontally disposed. The heating element 650 and a plurality of nanowires may be disposed on the same plane. The heating element 650 provide heat to both ends of the plurality of nanowires One end of the heating element 650 may be connected to the first electrode 300 for heating element which is connected to both ends of a plurality of nanowires 200 and may extend in the first direction to have a predetermined length. A second electrode 600 for heating element may be disposed at the other end of the heating element 650. One end of the second electrode 600 for heating element may be fixed to the substrate 100 by an anchor. The second electrode 600 may be referred to as an outer electrode. The suspended nanowire structure may include a plurality of the second electrodes 600. The second electrodes 600 may include a first outer electrode disposed at the other end of a first of the heating elements 650 and a second outer electrode disposed at the other end of a second of the heating elements 650.

The heating element 650 floats on the substrate 100 together with a plurality of nanowires 200.

The material of the heating element 650 may be a metal having excellent heat transfer. For example, the heating element 650 may be platinum (Pt), but is not limited thereto, and any material that can be used as the heating element may be used.

Although FIG. 11 shows the heating element 650 in a film form, this is schematically illustrated for simulation. As shown in FIG. 14, the heating element 650 may have a plurality of nanowires extending in the first direction arranged in the second direction. In FIG. 14, $I_s$ is a sensor measurement current, $V_s$ is a sensor measurement voltage, and $I_h$ is a heater heating current.

Figure 15:
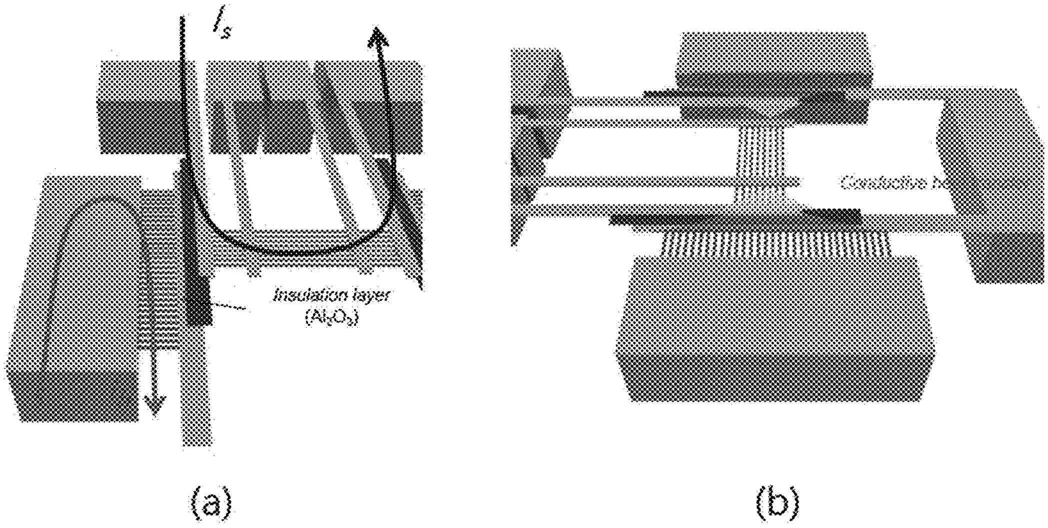
FIGS. 15(*a*) and (*b*) are views for explaining a driving method of the suspended nanowire structure shown in FIG. 14.

FIGS. 15(*a*) and (*b*) are views for explaining a driving method of the suspended nanowire structure shown in FIG. 14.

FIG. 15(*a*) is a diagram for explaining the operation mechanism. The operating mechanism heats the heating element 650 as a heater through the heater current $I_h$, and flows the sensor current $I_s$ to measure the resistance of the plurality of nanowires 200 as sensors. The heater current Ih and the sensor current Is are electrically separated by the insulator 700.

Referring to FIG. 15(*b*), the heat generated from the heated heating element 650 is transmitted through the first electrode 300, the insulator 700 and the measuring electrode 550 in the horizontal direction. It is transferred to the nanowire 200. At this time, it is preferable to design the first electrode 300 and the measuring electrode 550 to be long so that heat can be transferred well. The temperature distribution of the nanowire 200 as the sensor can be made uniform through the first electrode 300 and the measuring electrode 550.

Again, referring to FIGS. 11 to 12, A measurement electrode 550' is disposed on a plurality of nanowires 200, and extends along a second direction perpendicular to the first direction which is an extending direction of each nanowire 200. The measurement electrodes 550' are mode measurement electrodes. As shown in FIGS. 11 and 12, the measurement electrodes 550' may comprise of four measurement electrodes 550', for accurate measurement through point-probe measurement. In FIG. 11, the number of measurement electrodes 550' is illustrated as two first measurement electrodes 550*a* and two second measurement electrodes 550*b*, but is not limited thereto. For example, the measurement electrode 550' can be composed of combined two electrodes of one first measurement electrode 550*a* and one second measurement electrode 550*b*.

The suspended nanowire structure according to another embodiment of the present invention shown in FIGS. 10 to 11 generates heat by applying power in the order of a second electrode 600 for heating element, a heating element 650, a first electrode 300 for heating element, a plurality of nanowires 200, the first electrode for heating element, and the second electrode for heating element.

In the suspended nanowire structure according to another embodiment of the present invention shown in FIGS. 10 to 11, the heating element 650 and the plurality of nanowires 200 are not disposed in a vertical direction but are disposed in a horizontal direction.

Accordingly, in the suspended nanowire structure according to another embodiment of the present invention shown in FIGS. 10 to 11, a heating element 650 and a plurality of nanowires 200 which are gas sensing units are horizontally disposed. Thus, during driving, high temperature heat is provided right next to both ends of each nanowire 200. Therefore, a plurality of nanowires 200 may achieve a uniform temperature distribution as a whole. Accordingly, temperatures at both ends, which are portions having the lowest temperature in each nanowire 200, are increased by the heating element 650. Therefore, it is possible to improve the reaction rate to the gas.

Additionally, the suspended nanowire structure according to another embodiment of the present invention shown in FIGS. 11 to 12 may further include an insulator 700 covering a portion of the heating element 650 and the first electrode 300 for heating element and electrically insulating the first electrode 300 for heating element and the plurality of nanowires 200. One end portion of the plurality of nanowires 200 is disposed on one edge portion of the insulator 700. By this structure, the plurality of nanowires 200 may be supported by the insulator 700 to float. The insulator 700 may be made of a material capable of insulating electricity and also heat. For example, the insulator 700 may be aluminum oxide ($Al_2O_3$) or any material capable of electrically insulating. The insulator 700 may prevent heat loss from a portion of the heating element 650 and the first electrode 300 for heating element, thereby preventing the temperature of both ends of the plurality of nanowires 200 from being lowered.

Figure 13:
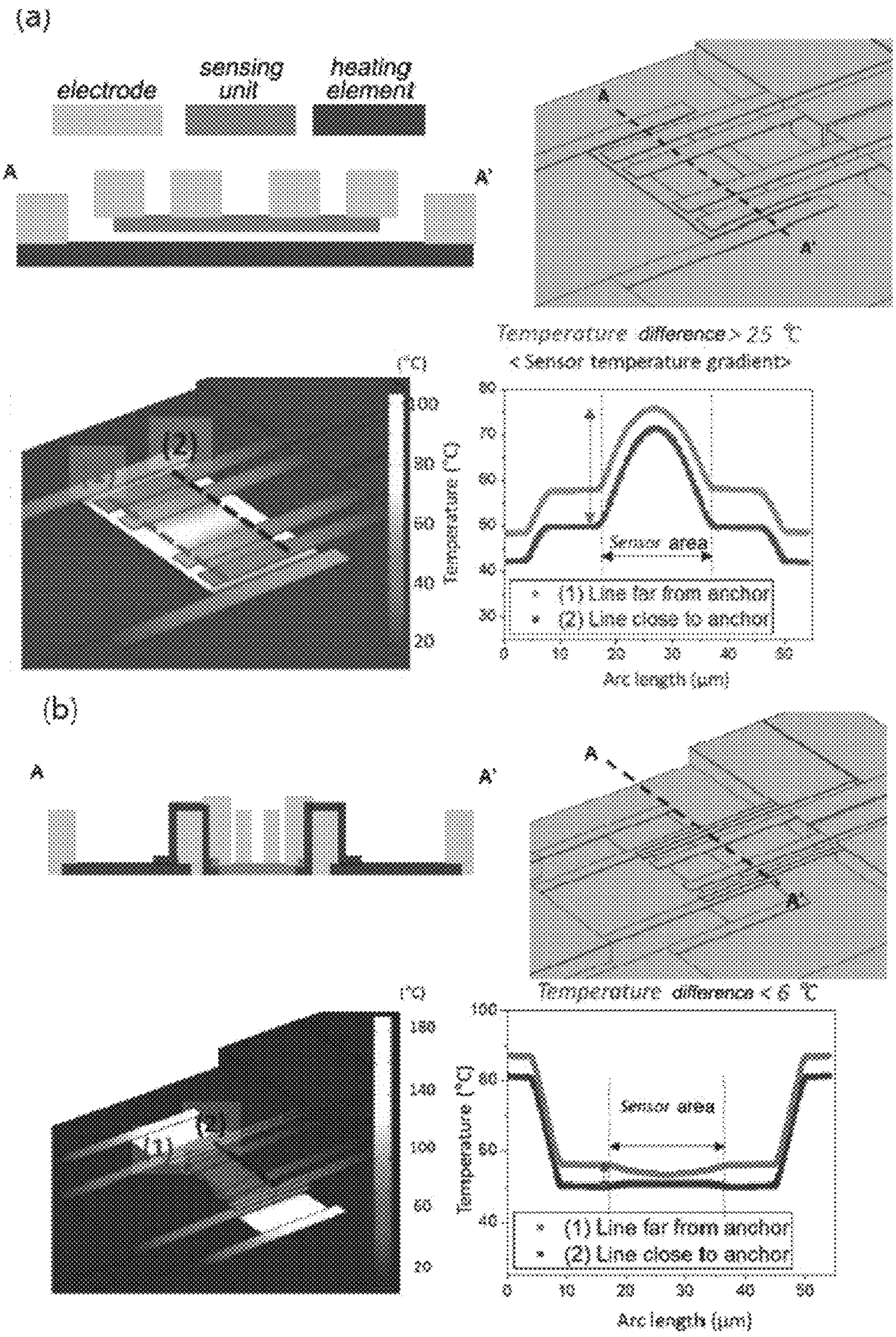
FIG. 13 is a view for comparing the effects of the conventional suspended nanowire structure with the suspended nanowire structure according to another embodiment of the present invention shown in FIGS. 11 to 12.

FIG. 13 is a view for comparing the effects of the conventional suspended nanowire structure with the suspended nanowire structure according to another embodiment of the present invention shown in FIGS. 11 to 12.

FIG. 13(*a*) illustrates a conventional vertically arranged suspended nanowire structure and simulation results thereof. Referring to FIG. 13(*a*), a heating element is disposed under a plurality of nanowires which are sensing units, and the nanowire and the heating element are configured in a vertical arrangement.

FIG. 13(*b*) shows a suspended nanowire structure in accordance with another embodiment of this invention illustrated in FIGS. 11 to 12, and its simulation results. Referring to FIG. 13(*b*), a plurality of nanowires which are sensing units and heating elements are horizontally disposed.

Referring to FIGS. 13(*a*) and 13(*b*), when the same heat is applied to the heating element, it can be confirmed that the plurality of nanowires of the suspended nanowire structure in accordance with another embodiment of the present invention have a significantly smaller temperature difference than the plurality of nanowires of the conventional suspended nanowire structure. Specifically, it may be seen that a temperature difference (maximum temperature-minimum temperature) of a sensor region was 25 degrees or more in a plurality of nanowires of a conventional suspended nanowire structure, but a temperature difference of the sensing region in the plurality of nanowires of the suspended nanowire structure according to another embodiment of the present invention is 6 degrees or less. According to these results, it may be understood that a reaction rate with respect to gas is improved more than in the prior art because the temperature distribution of the nanowire unit, which is a sensing unit, is generally uniform in the suspended nanowire structure according to another embodiment of the present invention.

Figure 16:
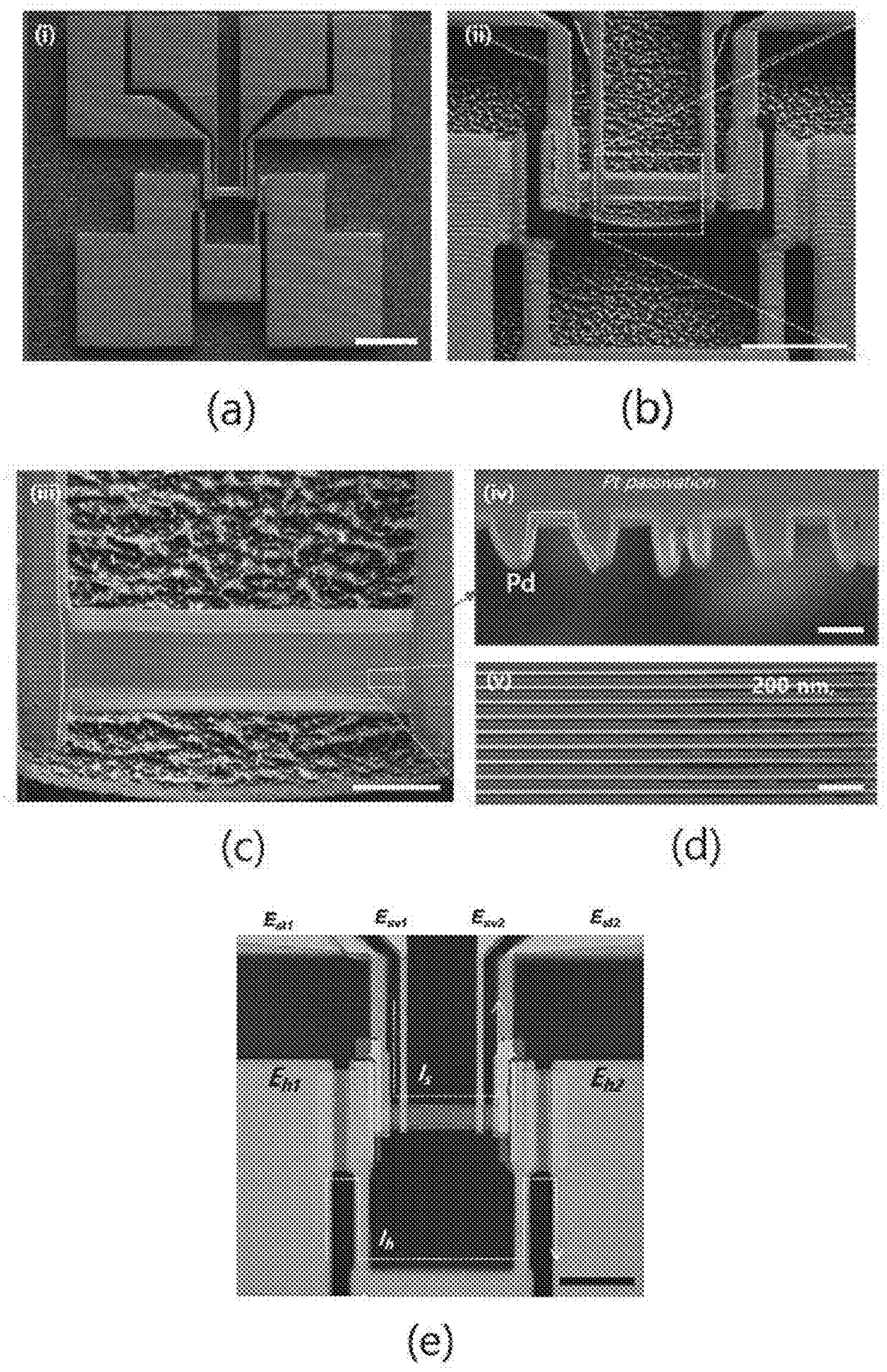
FIG. 16(*a*) to (*e*) are micrographs of actually fabricating the suspended nanowire structure shown in FIG. 14.

FIG. 16(*a*) to (*e*) are micrographs of actually fabricating the suspended nanowire structure shown in FIG. 14.

FIG. 16(*a*) to (*d*) are electron micrographs. FIG. 16(*b*) is an enlarged electron microscope of a part including a plurality of nanowires of FIG. 16(*a*), FIG. 16(*c*) is an enlarged electron microscope of a part of FIG. 16(*b*), and FIG. (d) is a cross-sectional photograph and an enlarged photograph of a part of FIG. 16(*c*).

FIG. 16(*e*) is a photomicrograph. In FIG. 16(*e*), $E_{sl1}$, $E_{sl2}$ are current applying electrodes for sensor measurement, $E_{sv1}$, $E_{sv2}$ are current applying electrodes for sensor measurement, $E_{h1}$, $E_{h2}$ are current applying electrodes for heating the heater, $I_s$ is the sensor current path, and $I_h$ is the heater current path.

Figure 17:
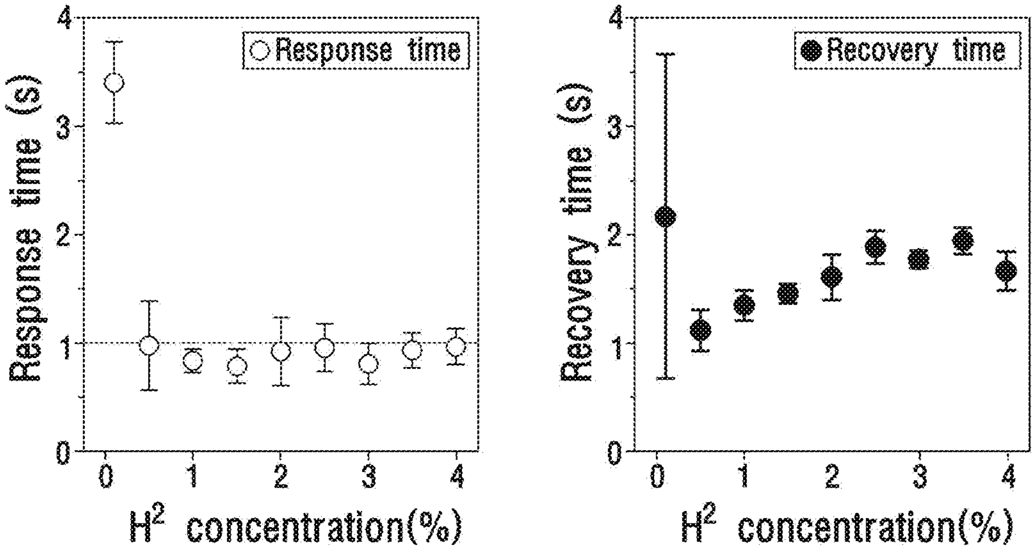
FIG. 17 is a Response time (left graph) and Recovery time (right side) according to the hydrogen concentration when a plurality of nanowires, which are sensors, are heated to a temperature of 65° C. in the suspended nanowire structure shown in FIG. 14.

FIG. 17 is a Response time (left graph) and Recovery time (right side) according to the hydrogen concentration when a plurality of nanowires, which are sensors, are heated to a temperature of 65° C. in the suspended nanowire structure shown in FIG. 14. Referring to the left and right graphs of FIG. 17, it can be confirmed that the reaction is fast enough to react with hydrogen gas within 1 second.

The suspended nanowire structure according to various embodiments of the present invention shown in FIGS. 9 to 17 has a novel structure that has not been present in the prior art. Specifically, in order to reduce the difference between the maximum temperature and the minimum temperature in consideration of the temperature distribution of each nanowire, the heating electrode is introduced in an embodiment of FIG. 9, and the heating element is introduced in another embodiment of FIG. 11. According to the two embodiments, the temperature distribution of the nanowires is uniform as a whole. Therefore, in particular, there is an advantage in that the reaction rate to gas is improved. In particular, the reaction rate for hydrogen gas can be designed within 1 second (Sec). Accordingly, the U.S DOE reference shown in FIG. 1 may be satisfied. Furthermore, temperature distribution acts as a key factor not only in hydrogen gas but also in other types of gas sensors. Therefore, embodiments of the present invention may also be used in various types of gas sensors.

In addition, the suspended nanowire structure according to various embodiments of the present invention shown in FIGS. 9 to 17 uses a top-down semiconductor process-based manufacturing process. Thus, it has high applicability because it can be uniformly produced with high reproducibility in a large area.

Features, structures, effects, etc. described in the embodiments are included in one embodiment of the present invention and are not necessarily limited to one embodiment. Furthermore, the features, structures, effects, and the like illustrated in each embodiment may be implemented in combination or modification with respect to other embodiments by a person skilled in the art to which the embodiments belong. Therefore, it should be interpreted that the contents related to these combinations and modifications are included in the scope of the present invention.

In addition, although the embodiment has been mainly described above, this is merely an example and this invention is not limited, and it will be appreciated by a person skilled in the art that various modifications and applications not illustrated are possible within the scope not departing from the present invention. For example, each component specifically shown in the embodiment may be modified and implemented. And differences related to these modifications and applications should be interpreted as falling within the scope of the present invention as defined in the appended claims.

EXPLANATION OF THE CODE

100: substrate
200: plurality of nanowires
300: electrode
450: heating electrode
550: measurement electrode
650: heating element

What is claimed is:

1. A suspended nanowire structure comprising:
a substrate;
a plurality of nanowires suspended above the substrate and extending along a first direction, the plurality of nanowires having a first end and a second end;
a first inner electrode disposed at the first end of the plurality of nanowires;
a second inner electrode disposed at the second end of the plurality of nanowires;
a first heating element having one end directly connected to the first inner electrode;
a second heating element having one end directly connected to the second inner electrode;
a first insulator that electrically insulates the first inner electrode from the plurality of nanowires;
a second insulator that electrically insulates the second inner electrode from the plurality of nanowires; and
at least two measurement electrodes, each of which is disposed on the plurality of nanowires, wherein:
the first inner electrode and the first insulator are located between the first heating element and the plurality of nanowires in the first direction,
the second inner electrode and the second insulator are located between the second heating element and the plurality of nanowires in the first direction, and
parts of each of the plurality of nanowires and the first and second heating elements are located in the same plane.

2. The suspended nanowire structure of claim 1, wherein:
the first insulator covers a portion of the first heating element;
one end portion of the plurality of nanowires is disposed on one edge portion of the first insulator.

3. The suspended nanowire structure of claim 2, wherein:
the plurality of nanowires are made of at least one of palladium (Pd), a Pd-metal alloy, or a Pd based compound,
the first and second heating elements are made of platinum, and
the first and second insulators are made of aluminum oxide.

4. The suspended nanowire structure of claim 1, wherein:
the at least two measurement electrodes extend in a second direction perpendicular to the first direction.

5. The suspended nanowire structure of claim 4, wherein:
the at least two measurement electrodes include a first measurement electrode disposed on the first end of the plurality of nanowires, and
the at least two measurement electrodes include a second measurement electrode disposed on the second end of the plurality of nanowires.

6. The suspended nanowire structure of claim 1, wherein:
the plurality of nanowires has a first surface and a second surface opposite to the first surface,
the first insulator and the second insulator are disposed on the first surface, and
the second surface is exposed to an outside of the suspended nanowire structure.

7. A suspended film structure comprising:
a substrate;
a film suspended above the substrate and extending along a first direction, the film having a first end and a second end;
a first inner electrode disposed at the first end of the film;
a second inner electrode disposed at the second end of the film,
a first heating element having one end directly connected to the first inner electrode;
a second heating element having one end directly connected to the second inner electrode;
a first insulator that electrically insulates the first inner electrode from the film;
a second insulator that electrically insulates the second inner electrode from the film; and
at least two measurement electrodes, each of which is disposed on the film, wherein:
the first inner electrode and the first insulator are located between the first heating element and the film in the first direction,
the second inner electrode and the second insulator are located between the second heating element and the film in the first direction, and
parts of each of the film and the first and second heating elements are located in the same plane.

8. The suspended film structure of claim 7, wherein:
the first insulator covers a portion of the first heating element;
one end portion of the film is disposed on one edge portion of the first insulator.

9. The suspended film structure of claim 8, wherein:
the film is made of at least one of palladium (Pd), a Pd-metal alloy, or a Pd based compound,
the first and second heating elements are made of platinum, and
the first and second insulators are made of aluminum oxide.

10. The suspended film structure of claim 7, further comprising:
the at least two measurement electrodes extend in a second direction perpendicular to the first direction.

11. The suspended film structure of claim 10, wherein:
the at least two measurement electrodes include a first measurement electrode disposed on the first end of the film, and
the at least two measurement electrodes include a second measurement electrode disposed on the second end of the film.

12. The suspended film structure of claim 7, wherein:

the film has a first surface and a second surface opposite to the first surface, the first insulator and the second insulator are disposed on the first surface, and the second surface is exposed to an outside of the suspended film structure.

* * * * *